United States Patent
Holler

(10) Patent No.: US 7,112,276 B2
(45) Date of Patent: Sep. 26, 2006

(54) CONTROLLED DOSING OF CHLORINE DIOXIDE OF OTHER SANITIZING AGENTS INTO PRESSURIZED WATER SYSTEMS

(75) Inventor: Thomas D. Holler, Glastonbury, CT (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/096,537

(22) Filed: Apr. 1, 2005

(65) Prior Publication Data

US 2005/0167349 A1 Aug. 4, 2005

Related U.S. Application Data

(63) Continuation of application No. 10/392,670, filed on Mar. 18, 2003, now Pat. No. 6,913,691.

(60) Provisional application No. 60/366,144, filed on Mar. 20, 2002.

(51) Int. Cl.
*C02F 1/50* (2006.01)

(52) U.S. Cl. .................. 210/198.1; 210/209; 210/206; 422/256; 422/261; 137/268

(58) Field of Classification Search ............. 210/198.1, 210/209, 443, 206, 266, 282, 192; 422/256, 422/266, 282, 283, 261; 137/268
See application file for complete search history.

(56) References Cited

U.S. PATENT DOCUMENTS

| | | | |
|---|---|---|---|
| 2,546,568 A | 3/1951 | Taylor | |
| 3,183,057 A | 5/1965 | Marks et al. | |
| 3,754,079 A | 8/1973 | Callerame | |
| 4,370,305 A * | 1/1983 | Affonso | 422/292 |
| 4,547,381 A | 10/1985 | Mason et al. | |
| 4,689,169 A | 8/1987 | Mason et al. | |
| 5,019,346 A * | 5/1991 | Richter et al. | 422/28 |
| 5,476,579 A | 12/1995 | Choi et al. | |
| 5,772,003 A | 6/1998 | Hunt | |
| 5,974,810 A | 11/1999 | Speronello | |
| 6,280,617 B1 * | 8/2001 | Brandreth, III | 210/206 |
| 6,913,691 B1 * | 7/2005 | Holler | 210/198.1 |
| 2001/0036421 A1 | 11/2001 | Speronello et al. | |
| 2004/0129627 A1 | 7/2004 | McGibbon | |

FOREIGN PATENT DOCUMENTS

| | | |
|---|---|---|
| EP | 0 919 269 A2 * | 6/1999 |
| WO | WO 01/60750 A2 * | 8/2001 |
| WO | WO 02/00332 A1 * | 1/2002 |
| WO | WO 02/00332 A2 | 1/2002 |

OTHER PUBLICATIONS

Bio-Cide International, Inc., "OLAS On-Line Activation System," Instruction Manual, US.

(Continued)

*Primary Examiner*—Duane Smith
*Assistant Examiner*—Douglas J. Theisen
(74) *Attorney, Agent, or Firm*—R. Thomas Payne

(57) ABSTRACT

A medium having a support structure configured for circulation of a fluid therein, such as a replaceable filter cartridge, including a sanitizing agent which contains one or more reactants that are chemically configured for delivering chlorine dioxide or other sanitizing agents in a controlled dose to sanitize, deodorize, and disinfect upon being wetted by the fluid and positioned in the medium support structure to be exposed to the fluid circulating therein.

20 Claims, 3 Drawing Sheets

OTHER PUBLICATIONS

Purogene Chlorine Dioxide Product Information, 11 pages, dated Apr. 1964 to Oct. 2000.
Sanogene Chlorine Dioxide Product Information, 6 pages, 1964.
Oxine Sanitizer Product Information, 19 pages, Sep. 1991.
Dripping Wet Water, Inc., Product Information, 9 pages.
Pristine, Chlorine Dioxide—Technical Report, Nov. 12, 2001, pp. 1-2.

* cited by examiner

CONTROLLED DOSING OF CHLORINE DIOXIDE OF OTHER SANITIZING AGENTS INTO PRESSURIZED WATER SYSTEMS

CROSS-REFERENCE TO RELATED APPLICATION(S)

The subject application is a continuation of U.S. patent application Ser. No. 10/392,670, filed Mar. 18, 2003 now U.S. Pat. No. 6,913,691, which claims the benefit of priority to U.S. Provisional Patent Application No. 60/366,144, filed Mar. 20, 2002, the disclosure of each is herein incorporated by reference in its entirety.

BACKGROUND OF THE INVENTION

The subject invention relates to a system and method of water treatment, and more particularly, to systems and methods of delivering controlled doses of chlorine dioxide or other sanitizing agents into a pressurized water system.

Potable water contains various levels of background contaminants such as HPC, pathogenic bacteria and algae, even after municipal treatment. In most instances, chlorine is used to reduce the concentration of such background contaminants. Chlorine and chlorine compounds used for sanitization or disinfection are often removed from water supplies prior to use in drinking water systems, food service beverage systems and ice dispensing equipment. The reasons for removal vary depending on the application or system. For example, the presence of chlorine in the water supply to certain beverage systems may negatively impact a particular quality of the beverage product, such as its taste.

There are also a significant amount of downstream potable water systems that do not use disinfection chemicals. This results in increased levels of microorganisms and biofilm build-up. The build-up increases within dechlorination filters, resin beds, and other finely divided media filters during periods of stagnation. The build-up can be released downstream at high levels causing health concerns, as well as severe off-tastes and odors. Over a prolonged period of time biofilm coats water lines and wetted parts of dispensing equipment, thus compounding the problem.

The concern generated by known high levels of microorganism build-up has caused many in the food service and drinking water industry to periodically sanitize water lines, often reaching the threshold allowable by state or local regulations. Many of the sanitization procedures currently available are difficult to administer, costly, service intensive and use highly toxic chemicals. Some of the chemicals typically used in these procedures include peroxide, chlorine derivatives, muric acid and citric acid. Although the desired sanitizing effect may be achieved by these procedures, they are seldom implemented due to the aforementioned problems.

Chlorine dioxide or other sanitizing agents have also been found to be highly effective as a sanitizer for use in potable water lines. Prior treatment procedures employed a highly concentrated solution of chlorine dioxide or other sanitizing agents, which is formed independently in a remote container and then pumped into the system lines. This solution is allowed to remain in the system lines for extended periods of time while the pressure in the water line is shut off.

One of the primary disadvantages of using chlorine dioxide or other sanitizing agents as a sanitizer according to prior treatment procedures is the economic cost associated with the resulting system downtime since the system being sanitized is unusable during the treatment. Also, due to the toxic nature of the chlorine dioxide or other sanitizing agents solution, a specially trained service technician is often required to remain on-site until the solution is completely flushed out, thus further adding to the financial burden associated with these prior treatment procedures.

The flushing process itself often significantly extends the system downtime of the prior treatment procedures because of a residue left in the system lines by the prolonged static exposure to the chlorine or other sanitizing agents solution. This residue is often difficult to remove, and even low levels of such residue may be considered toxic or noxious, thus requiring the repeated flushing of the system.

It would be beneficial therefore, to provide a system and method for delivering controlled doses of chlorine dioxide or other sanitizing agents into a pressurized water system, which overcomes the deficiencies of the prior art.

SUMMARY OF THE DISCLOSURE

The present invention provides new and useful systems and methods for delivering controlled doses of chlorine dioxide or other sanitizing agents into a pressurized potable water system which overcomes the problems associated with the prior art.

A medium having a support structure with an inlet configured for receiving a fluid, an outlet configured for delivering a fluid and a body configured for circulating a fluid therein, such as a replaceable filter cartridge, which includes a sanitizing agent containing one or more reactants that are chemically configured for releasing a compound having sanitizing properties, such as chlorine dioxide, in a controlled dose upon being wetted by the fluid and positioned within the medium to be exposed to the fluid circulating therein.

Preferably, the sanitizing agent releases chlorine dioxide or other sanitizing agents in specific amounts, at a specific and controlled constant rate, to sanitize, deodorize, and disinfect equipment pipes connected to the medium outlet. The rate of chlorine dioxide or other sanitizing agents release would be set to dilute in water with a constant flow rate for a duration equivalent to perform the desired task, such as sanitize, deodorize, or disinfect water lines and equipment wetted parts.

The preferred mediums to be used in accordance with the present invention include systems or disposable cartridges. In particular, the present invention, is directed to a system for delivering a sanitizing agent to a fluid, which includes a substantially hollow vessel and a sanitizing agent having one or more reactants which are chemically configured to release a compound having sanitizing properties upon exposure to the fluid. The hollow vessel includes an inlet passage configured for receiving fluid flow, an outlet passage configured for fluid egress, and an interior chamber configured for receiving fluid from the inlet passage and providing temporary confinement of the fluid therein prior to egress from the outlet passage. The sanitizing agent is disposed in the chamber and the confinement of water therein may be provided by an independent valve.

The present invention is also directed to a filter cartridge that includes a hollow housing with a filter media chamber defined therein and a sanitizing agent disposed in the filter media chamber. The sanitizing agent preferably includes one or more reactants which are chemically configured to release a compound having sanitizing properties upon exposure to the fluid in the filter media chamber.

There can be inlet passage in the housing configured to provide fluid communication with the chamber and an outlet passage in the housing configured to provide fluid communication with the chamber. The fluid is directed to the inlet passage and flows through the filter media chamber, exiting the outlet passage with chlorine dioxide or other sanitizing agents from a portion of fluid included therewith having been exposed to the sanitizing agent in the filter media chamber.

Preferably, the fluid is water and the compound is chlorine dioxide or other sanitizing agents, in which case, the one or more reactants can include a chlorite and the release of chlorine dioxide or other sanitizing agents is initiated by contact with the water. The chlorite may be an aqueous soluble chlorite selected from the group consisting of sodium chlorite and potassium chlorite and mixtures thereof. Preferably, the one or more reactants include an aqueous soluble chlorite and an aqueous soluble acid. Preferably, the aqueous soluble acid is selected from the group consisting of phosphoric acid, fumaric acid, glycolic acid, acetic acid, ascorbic acid, oxalic acid, maleic acid, lactic acid, tartaric acid, citric acid and mixtures thereof.

In addition, the system or filter cartridge of the present invention may also include a filtration media disposed in the chamber along with the sanitizing agent. The filtration media may be configured to provide chemical or mechanical filtration depending on the application. Preferably, the filtration media and sanitizing agent are disposed in the chamber and configured so that fluid entering the chamber is first exposed to the filtration media prior to being exposed to the sanitizing agent and exiting the outlet.

In another embodiment which can be implemented in any medium (e.g., cartridge or system) constructed in accordance with the present invention, a solution may be disposed in the chamber that includes a second compound having sanitizing properties, such as chlorine. This solution is then mixed with fluid flowing in the chamber and exits through the outlet passage.

In yet another embodiment which can be implemented in any medium constructed in accordance with the present invention, a substantially hollow neck is mated with the chamber. The neck has an inlet port in fluid communication with an inlet passage that is configured to be in fluid communication with the chamber, and an outlet port in fluid communication with an outlet passage that is also configured to be in fluid communication with the chamber. The inlet passage and outlet passage are both disposed in the neck and configured to provide dual fluid flow within the neck and independent fluid communication with the chamber.

The aforementioned embodiment may further include a tubular member disposed axially in the neck and having a portion with a porous periphery extending into the chamber. The tubular member defines an inner axial passage therein and a radially outer axial passage bounded by the periphery of the tubular member and inner surface of the neck. Thus, the outer axial passage and the inner axial passage can provide the inlet and outlet passages, respectively. A filtration media may be disposed along the porous periphery of the portion of the tubular member extending into the filter media chamber and the sanitizing agent can be disposed within the inner axial passage of the portion of the tubular member extending into the chamber. Preferably, the sanitizing agent is separated from the filtration media by an inert porous divider.

In yet another embodiment which can be implemented in any medium constructed in accordance with the present invention, a second outlet port may be added to the housing or vessel at a position where it will be in fluid communication with the chamber, and adjacent relative to the position of the sanitizing agent within the chamber, so that a majority or substantially all of the fluid exposed to the sanitizing agent exits this second outlet.

Further features of the subject invention will become more apparent from the detailed description of the present invention that follows taken in conjunction with the drawings.

BRIEF DESCRIPTION OF THE DRAWINGS

So that those having ordinary skill in the art to which the present application appertains will more readily understand how to make and use the same, reference may be had to the drawings wherein.

These and other features of the subject invention will become more readily apparent to those having ordinary skill in the art from the following description of the preferred embodiment.

DETAILED DESCRIPTION OF THE DISCLOSURE

In the following detailed description of the present invention, references are made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. The following detailed description is, therefore, not to be taken in a limiting sense, and the scope of the present invention is defined by the appended claims and equivalents thereof.

The present invention provides vehicles, such as replaceable filter cartridges, for delivering chlorine dioxide or other sanitizing agents to a water system in a variety of controlled doses periodically by exposure of the water in the system to sanitizing or cleaning agents. These agents may include stable dry chemicals such as, but not limited to, those which are disclosed in the herein incorporated Published International Patent Application WO 01/60750A3 (PCT/US01/05002), capable of generating chlorine dioxide or other sanitizing agents when wetted. Preferably, the agent or agents release a specific amount of chlorine dioxide or other sanitizing agents, at a specific and controlled constant rate. The rate of chlorine dioxide or other sanitizing agents release would be set to dilute in water with a constant flow rate for a duration equivalent to clean (sanitize) water lines and equipment wetted parts.

Figure 1:
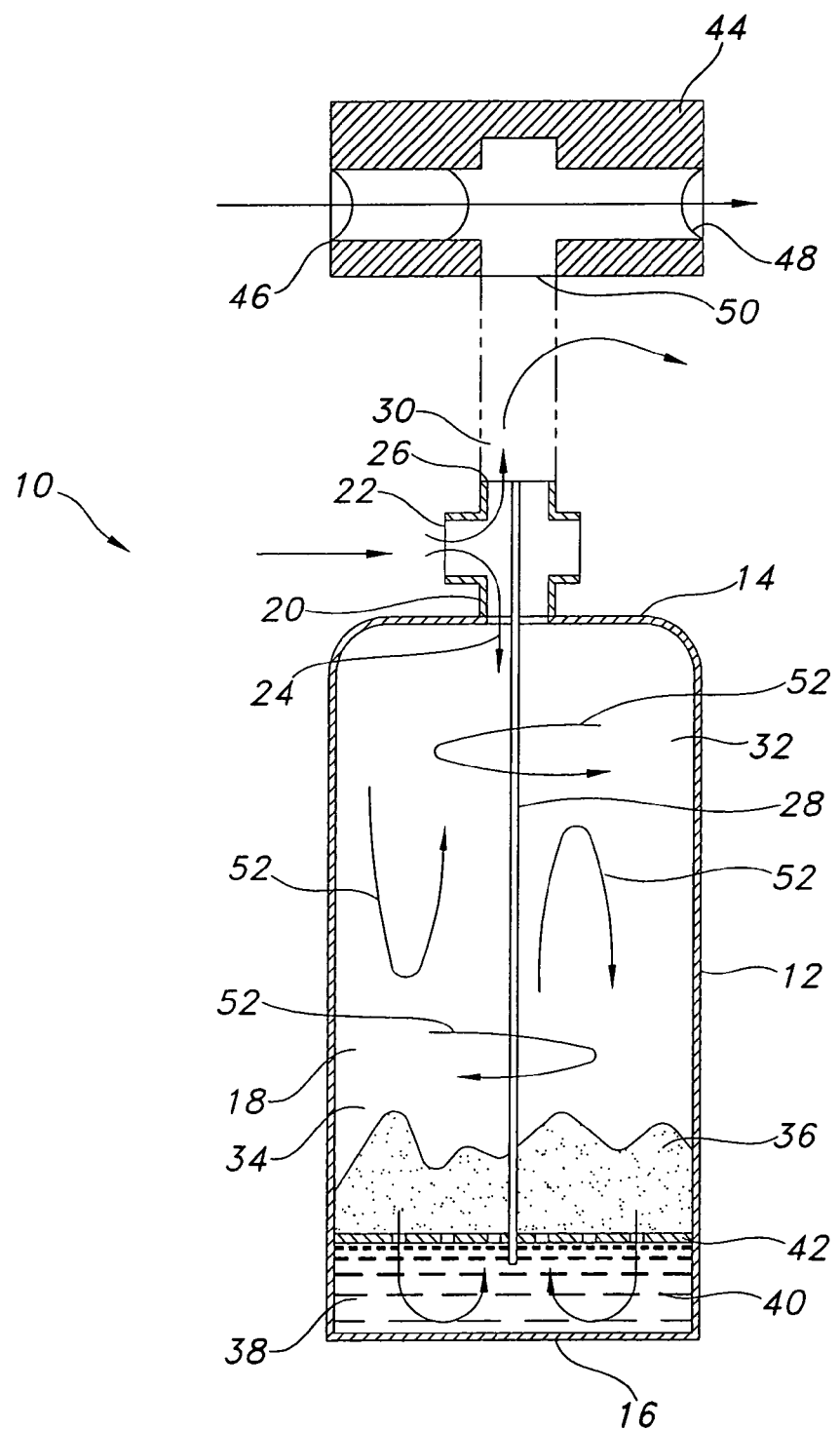
FIG. 1 is a representative illustration of a system for providing controlled dosing of chlorine dioxide or other sanitizing agents to sanitize and clean equipment pipes or lines constructed in accordance with a preferred embodiment of the present invention, which depicts the system including a dry sanitizing agent, which releases chlorine dioxide or other sanitizing agents upon wetting with water, and a liquid sanitizing agent and a filter head for connecting the system with the equipment.

Referring now to the drawings wherein like reference numerals identify similar structural features of the invention, there is illustrated in FIG. 1, a representative depiction of a stand-alone type system for providing controlled dosing of sanitizer/cleaner into pressurized water systems which is constructed in accordance with a preferred embodiment of the subject invention and designated generally by reference numeral 10.

System 10 includes a pressure vessel 12 having a first end 14 and a second end 16 defining a hollowed out, generally cylindrical chamber 18 therein. First end 14 has a neck 20 which has an inlet port 22 in fluid communication with an inlet passage for directing fluid flow into chamber 18 according to arrow 24 (hereinafter referred to as "inlet passage 24"). Neck 20 also includes an outlet port 26 in fluid communication with an outlet tube 28 which extends axially into chamber 18. In this embodiment, neck 20 also includes an optional bypass passage which provides fluid communication between inlet passage 24 and outlet port 26 in accordance with arrow 30 (hereinafter referred to as "bypass passage 30"). Chamber 18 includes an unfilled region 32 adjacent first end 14, a first treatment region 34 containing a dry sanitizing agent 36 with controlled reaction dissolution and a second treatment region 38 containing a concentrated sanitizing liquid 40 adjacent second end 16. First treatment region 34 and second treatment region 38 are separated from each other by a porous inert divider 42. Sanitizing liquid 40 is preferably chlorine and may also include a dye indicator for facilitating awareness of its exhaustion.

System 10 is attachable to the water supply line (not shown) to a master system (not shown), such as a beverage preparation device or ice making machine, via a filter head 44 having a first line 46 for receiving fluid from a supply line (not shown), a second line 48 for providing fluid to the master system and a treatment device port 50. Filter head 44 may be constructed with or retrofitted onto the supply line or any other lines in the master system. System 10 may also be connected to the master system in other ways, such as by a permanent connection having flow control valves. Treatment device port 50 separates first line 46 and second line 48 and to provide a space in which neck 20 of system 10 may be inserted. Filter head 44 may also include a line pressure bypass with constant flow rate. The flow rate may vary depending on the application but typically ranges from about 0.25 gallons per minute to about 5.0 gallons per minute.

Preferably, the outer periphery of neck 20 and the inner surface of treatment device port 50 are configured to be engaged by corresponding cooperative structures defined respectively thereon. The cooperative structures may consist of a proprietary interconnection. Also, it is preferable that neck 20 and treatment device port 50 be sealingly engaged (e.g., using water resistant sealing rings fabricated of an elastomeric material) to maintain the integrity of fluid communication between the first line 46 and inlet port 22, and between outlet port 26 and second line 48, respectively.

Once system 10 is installed in filter head 44 (i.e., neck 20 is engaged with treatment device port 50), water is provided to first line 46 and allowed to enter inlet port 22. A portion of the water flow entering inlet port 22 will travel through inlet passage 24 into chamber 18 while the remaining portion of water flow will travel through bypass passage 30. Bypass passage 30 is configured to direct the water flowing therein through outlet port 26 sans treatment, to be diluted with the treated water also exiting from outlet port 26. The water flowing through inlet passage 24 pours into unfilled region 32 of chamber 18 creating turbulence as indicated by arrows 52 which facilitates better mixing of the untreated water and greater contact with the sanitizers in treatment regions 34 and 38 within chamber 18.

The pressure of the incoming flow forces water within unfilled region 32 through first treatment region 34, porous divider 42, and second treatment region 38 before exiting chamber 18 via outlet tube 28. As the water passes through treatment regions 34 and 38, it is exposed to dry sanitizing agent 36 and concentrated sanitizing liquid 40. The flow from outlet tube 28 mixes with untreated water flowing from outlet 26 via bypass passage 30 (if included) before being directed to the master system via second line 48 in filter head 44. Preferably, for this embodiment, the water flowing to the master system contains about 0.1 parts per million of sanitizer to about 10 parts per million of sanitizer after passage through system 10.

Figure 2:
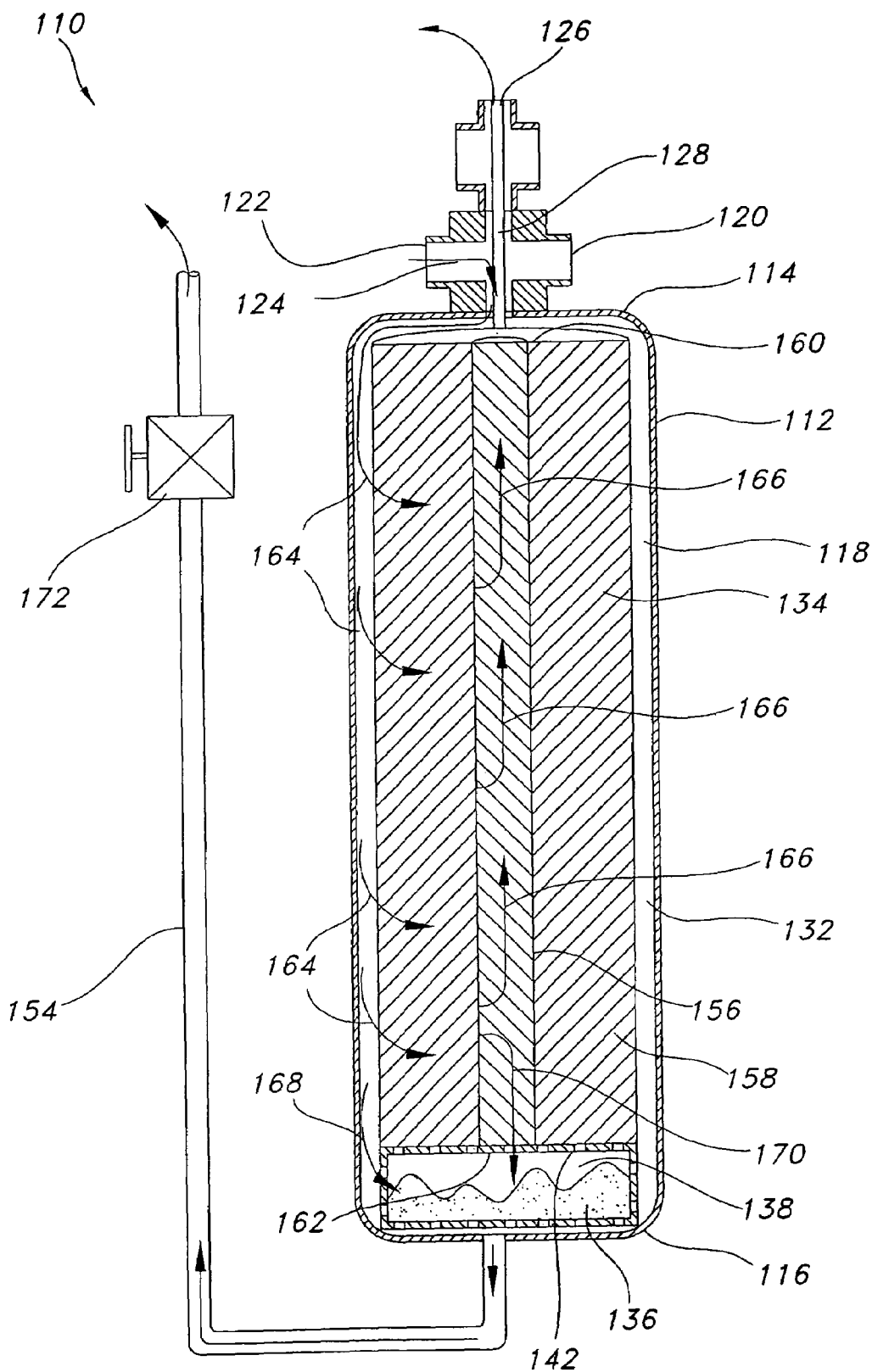
FIG. 2 is a representative illustration of a filter cartridge for providing controlled dosing of chlorine dioxide or other sanitizing agents to sanitize and clean equipment pipes or lines constructed in accordance with a preferred embodiment of the present invention, including a dry sanitizing agent, which releases chlorine dioxide or other sanitizing agents upon wetting with water, a filtration media, a first outlet for water exposed to the filtration media, and a second outlet for providing water exposed to the sanitizing agent.

Another preferred embodiment of the present invention is represented by the depiction in FIG. 2 of a filter cartridge having a separate sanitizer stream for providing controlled dosing of sanitizer/cleaner into pressurized water systems, which is constructed in accordance with the subject invention and designated generally by reference numeral 110.

System 110 includes a filter cartridge housing 112 having a first end 114 and a second end 116 defining a hollowed out, generally cylindrical chamber 118 therein. First end 114 has a neck 120 which has an inlet port 122 in fluid communication with an inlet passage for directing fluid flow into chamber 118 according to arrow 124 (hereinafter referred to as "inlet passage 124"). Neck 120 also includes an outlet port 126 in fluid communication with an outlet tube 128 extending axially into chamber 118. In this embodiment, filter cartridge housing 112 also includes a separate sanitizer line 154 that draws fluid from chamber 118 adjacent second end 116 of filter cartridge housing 112.

Chamber 118 includes an axially disposed, radially porous center core 156 and radially outer first treatment region 134 containing a filtration media 158 adjacent first end 114, which may be mechanical or chemical in nature (e.g., a peat block, screen, activated carbon block, sediment block, granular media, etc.), and which substantially surrounds center core 156. Center core 156 includes a first open axial end 160 adjacent to first end 114 of filter cartridge housing 112 and a second open axial end 162 adjacent to second end 116 of filter cartridge housing 112.

The second open end 162 of center core 156 is adjacent to a second treatment region 138 containing a dry sanitizing agent 136 with controlled reaction dissolution. First treatment region 134 and second treatment region 138 are separated by a porous inert divider 142. In addition, filtration media 158 is configured and dimensioned to fit within filter cartridge housing 112 to define an unfilled annular region 132 between the inner circumferential surface of chamber 118 and the outer periphery of filtration media 158 for fluid flow therebetween, as illustrated by arrows 164.

Filter cartridge 110 is attachable to a supply line (not shown), preferably located within the housing of a master system (not shown), such as a beverage preparation device or ice making machine. This may be accomplished via a filter head (not shown) as in the previous embodiment or other connection having a port configured to engage neck 120.

When system 110 is in use, water pumped through the supply line enters inlet port 122 and flows into chamber 118 through inlet passage 124 in neck 120 of filter cartridge housing 112. As illustrated by arrows 164, the water flows through the unfilled annular region 132 and is pushed radially inward by the fluid pressure created in cartridge housing 112. The water is forced through filtration media 158 and into center core 156. A portion of the water flow in center core 156 is directed towards first end 114 and into outlet tube 128, eventually exiting filter cartridge housing 112 through outlet port 126, as illustrated by arrows 166. Preferably, the majority of the water flow follows the path shown by arrows 166.

A portion of the water entering unfilled annular region 132 flows axially toward second end 116 in chamber 118 and into second treatment region 138 through porous inert divider 142 without passing through filtration media 158, as illustrated by arrow 168. A portion of the water flow in center core 156 which has passed through filtration media 158 is directed by pressure, or lack thereof, toward second end 116. This flow of treated water exits center core 156 from second open end 162 and enters into second treatment region 138 through porous inert divider 142, as illustrated by arrow 170. Water flowing within second treatment region 138 contacts dry sanitizing agent 136 and then exits filter cartridge housing 112 through separate sanitizer line 154. The water exposed to dry sanitizing agent 136 may be controlled by a control valve 172 in sanitizer line 154.

Figure 3:
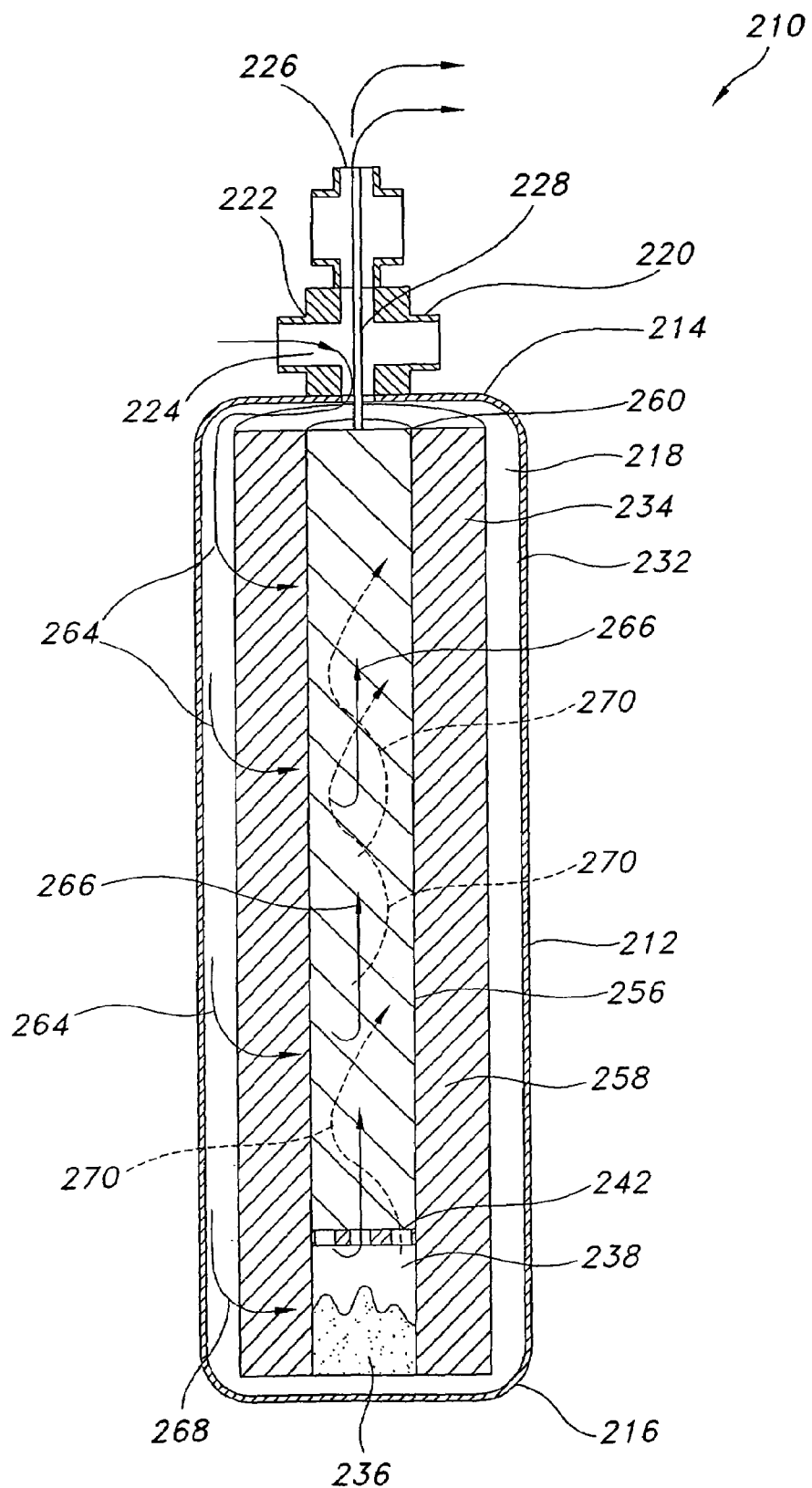
FIG. 3 is a representative illustration of a filter cartridge for providing controlled dosing of chlorine dioxide or other sanitizing agents to sanitize and clean equipment pipes or lines constructed in accordance with a preferred embodiment of the present invention, including a dry sanitizing agent, which releases chlorine dioxide or other sanitizing agents upon wetting with water and a filtration media, wherein the outlet stream from the filter cartridge contains a blend of water exposed to the filtration media and water exposed to the sanitizing agent.

Another preferred embodiment of the present invention is represented by the depiction in FIG. 3 of a filter cartridge having an encapsulated sanitizing agent for providing controlled dosing of sanitizer/cleaner into pressurized water systems, which is constructed in accordance with the subject invention and designated generally by reference numeral 210.

System 210 includes a filter cartridge housing 212 having a first end 214 and a second end 216 defining a hollowed out, generally cylindrical chamber 218 therein. First end 214 has a neck 220 which has an inlet port 222 in fluid communication with an inlet passage for directing fluid flow into chamber 218 according to arrow 224 (hereinafter referred to as "inlet passage 224"). Neck 220 also includes an outlet port 226 in fluid communication with an outlet tube 228 extending axially into chamber 218.

Chamber 218 includes an axially disposed, radially porous center core 256 and radially outer first treatment region 234 containing a filtration media 258 that extends axially substantially from first end 214 to second end 216 and substantially surrounds center core 256. Filtration media 258 is configured and dimensioned to provide an unfilled annular region 232 between the inner circumferential surface of chamber 218 and the outer periphery of filtration media 258 for fluid flow therebetween, as illustrated by arrows 264.

Filtration media 258 may be mechanical or chemical in nature (e.g., a peat block, screen, activated carbon block, sediment block, granular media, etc.).

Center core 256 includes an open axial end 260 adjacent to first end 214 of filter cartridge housing 212 and a second treatment region 238 containing a dry sanitizing agent 236 with controlled reaction dissolution adjacent to second end 216 of filter cartridge housing 212. An axially disposed porous inert divider 242 separates second treatment region 238 from the remaining portion of center core 256.

Filter cartridge 210 is attachable to a supply line (not shown), preferably located within the housing of a master system (not shown), such as a beverage preparation device or ice making machine. This may be accomplished via a filter head (not shown) as in the previous embodiments or other connection having a port configured to engage neck 220.

In use, water is pumped through supply line and flows from inlet port 222 to chamber 218 through inlet passage 224 in neck 220 of filter cartridge housing 212. As illustrated by arrows 264, the water flows through the unfilled annular region 232 and is pushed radially inward by fluid pressure. Water is forced through filtration media 258 and into center core 256, where it makes its way into outlet tube 228 and exits cartridge housing 212 through outlet port 226, as illustrated by arrows 266.

A portion of the water flow forced through filtration media 258 also enters second treatment region 238 and contacts dry sanitizing agent 236, as illustrated by arrow 268. The water exposed to dry sanitizing agent 236 flows through porous inert divider 242, as shown by arrows 270, where it mixes with water which has not been treated by dry sanitizing agent 236 before exiting filter cartridge housing 212, as described above.

Preferably, predetermined amounts of dry sanitizing agent 236 is encapsulated in a sanitary cartridge such as cartridge 110 and 210, in a way, that would allow the full flow of fluid therethrough. A suitable encapsulated sanitary cartridge configuration is manufactured by Cuno Incorporated of Meriden, Conn., and sold under the tradename SQC® series drinking water system.

System 10 and cartridges 110 and 210, or other similar devices constructed in accordance with the present invention, may have a variety of end connector configurations to fit existing filter systems for periodic insertion and activation, as well as proprietary interconnects. A system or cartridge constructed in accordance with the present invention can also be incorporated into master system downstream of any absorbent media and can be removed or left in place until replaced for another treatment depending upon the filter head configuration. Furthermore, a system or cartridge of the present invention can be a standard component, which would be either supplied as part of a new installation, as a retrofit or as a replacement medium for chlorine dioxide or other sanitizing agents dosing.

Various doses of chlorine dioxide or other sanitizing agents may be administered via the systems and cartridges of the present invention. For example, the periodic high dosing of chlorine dioxide or other sanitizing agents may be accomplished by utilizing predetermined amounts of a sanitizing agent that also allows full flow through the cartridge. Once installed, water can be introduced into a system or cartridge of the present invention is filled with the outlet port restricted. Once wetted the agent would generate chlorine dioxide or other sanitizing agents within the cartridge for a predetermined period of time, until a high level (e.g., 50 parts per million to 100 parts per million) is dissolved into the water in the system or cartridge chamber. The outlet port may be opened when ready and the chlorine dioxide or other sanitizing agents rich water can be forced by water pressure downstream into the water lines and equipment wetted parts, thereby stripping biofilm therefrom.

The concentrated solution may be allowed to reach all exit ports of the downstream equipment. Thereafter, the outlet line of the master system can be shut off. The chlorine dioxide or other sanitizing agents rich solution may be held for a predetermined amount of time (e.g., from twenty minutes to several hours) to facilitate the stripping of biofilm build-up in the master system lines and sanitize the water and wetted equipment parts. The master system can then be flushed for a prescribed amount of time so as to clear the water lines and cartridge of any remaining chlorine dioxide or other sanitizing agents residue. One of the advantages of using chlorine dioxide or other sanitizing agents is its powerful oxidation capabilities and the ease by which residue is flushed out of the system.

For high dosing as described above, the rate of chlorine dioxide or other sanitizing agents generation is rapid, but its release from the cartridge or stand alone system can be set to dilute in water with a constant flow rate, preferably between 50 parts per million and 100 parts per million, for a duration equivalent to fill water lines and equipment wetted parts.

Low doses of chlorine dioxide or other sanitizing agents (i.e., about 0.1 parts per million to about 0.5 parts per million) can also be delivered into the water system periodically by exposure of the water in the system to sanitizing or cleaning agents contained in a system or cartridge constructed in accordance with the present invention. For example, a low-level chlorine dioxide or other sanitizing agents dosing agent may be incorporated into a cartridge, such as cartridge 210, which are constructed in accordance with the present invention, along with other reduction, removal or absorptive capabilities, or combinations thereof. Upon installation, the agent can generate chlorine dioxide or other sanitizing agents at a low controlled rate for a short duration. Preferably, the chlorine dioxide or other sanitizing agents generation occurs at a location that is downstream of any absorbent media within the same cartridge. As water enters the filter cartridge, chlorine dioxide or other sanitizing agents generation begins. The absorbent and reduction media would perform as normal for their prescribed life (e.g., 3 months, 6 months or 1 year), while the chlorine dioxide or other sanitizing agents generation would end within the first few minutes of use (e.g., from about 5 to about 20 minutes). The net result would be the periodic sanitization of water lines and equipment wetted parts with the convenience of a standard cartridge replacement.

In addition, a system or cartridge constructed in accordance with the present invention provides for the safe transportation and handling of chlorine dioxide or other sanitizing agents producing agents, controlled low level dosing rate in a dynamic flowing condition, controlled dosing duration, and system or cartridge formats and head assemblies which can introduce chlorine dioxide or other sanitizing agents into a pressurized water line.

While the present invention has been described with respect to preferred embodiments, those skilled in the art will readily appreciate that various changes and/or modifications can be made to the present invention with departing from the spirit or scope of the invention. For example, a filter cartridge may be constructed having a sanitizing agent in accordance with the present invention and with a bypass feature such as, but not limited to, those filter cartridges which are disclosed in the herein incorporated, copending and commonly owned U.S. patent application Ser. No. 10/337,832 filed on Jan. 7, 2003.

What is claimed is:

1. A system for delivering controlled doses of a sanitizing agent to a fluid, comprising:
   a substantially hollow vessel having an inlet passage configured for receiving fluid flow, an outlet passage configured for fluid egress, and an interior chamber configured for receiving fluid from the inlet passage and providing temporary confinement of the fluid therein prior to egress from the outlet passage;
   at least one sanitizing agent operatively disposed in the chamber, the sanitizing agent including one or more reactants which are chemically configured to release a compound having sanitizing properties upon periodic exposure to the fluid in the chamber; and
   a solution disposed in the chamber of the vessel including chlorine, wherein the solution is mixed with fluid in the chamber for egress through the outlet passage.

2. A system as recited in claim 1, wherein the compound is chlorine dioxide.

3. A system as recited in claim 1, wherein the fluid is water.

4. A filter cartridge comprising:
   a hollow housing with a filter media chamber defined therein;
   a substantially hollow neck mated with the filter media chamber having an inlet port in fluid communication with an inlet passage configured to be in fluid communication with the filter media chamber and an outlet port in fluid communication with an outlet passage configured to be in fluid communication with the filter media chamber, wherein the inlet passage and outlet passage are disposed in the neck and configured to provide dual fluid flow within the neck and independent fluid communication with the filter media chamber;
   a sanitizing agent disposed in the filter media chamber, the sanitizing agent including one or more reactants which are chemically configured to release a compound having sanitizing properties upon exposure to the fluid in the filter media chamber; and
   a dye indicator operatively associated with the sanitizing agent, for facilitating awareness of the presence of the sanitizing agent in the fluid at a location remote from the filter cartridge and the subsequent exhaustion thereof from the fluid at the location remote from the filter cartridge, the filter cartridge being operatively positioned in a pressurized fluid system.

5. The system of claim 4, wherein the compound is chlorine dioxide.

6. The system of claim 4, wherein the fluid is water.

7. The system of claim 6, wherein the one or more reactants include an aqueous soluble chlorite and an aqueous soluble acid.

8. The system of claim 6, further comprising a filtration media disposed in the filter media chamber.

9. The system of claim 8, wherein the filtration media is substantially fabricated of activated carbon.

10. The system of claim 8 wherein the filtration media and sanitizing agent are disposed in the filter media chamber so that fluid entering therein is first exposed to the filtration media prior to the sanitizing agent.

11. The system of claim 4, further comprising a tubular member disposed axially in the neck and having a portion with a porous periphery extending into the filter media chamber, the tubular member defining an inner axial passage therein and a radially outer axial passage bounded by the periphery of the tubular member and inner surface of the neck, wherein the outer axial passage and the inner axial passage provide the inlet and outlet passages, respectively.

12. The system of claim 11, further comprising a filtration media disposed along the porous periphery of the portion of the tubular member extending into the filter media chamber.

13. A filter cartridge, comprising:
a housing having a filter media chamber defined therein;
an inlet passage in the housing configured to provide fluid communication with the filter media chamber;
an outlet passage in the housing configured to provide fluid communication with the filter media chamber;
a sanitizing agent disposed in the filter media chamber, the sanitizing agent including one or more reactants which are chemically configured to release Chlorine dioxide or other sanitizing agents upon exposure to water, and
a dye indicator operatively associated with the sanitizing agent, for facilitating awareness of the presence of the sanitizing agent in the water at a location remote from the filter cartridge and the subsequent exhaustion thereof from the water at the location remote from the filter cartridge, the filter cartridge being operatively positioned in a pressurized water system;
wherein water being directed to the inlet passage flows through the filter media chamber and exits the outlet passage with the sanitizing agent from a portion of water included therewith having been exposed to the sanitizing agent in the filter media chamber.

14. A filter cartridge as recited in claim 13, wherein the concentration of chlorine dioxide in the water flowing from the outlet passage ranges from about 0.1 ppm to about 10 ppm.

15. A system for delivering a sanitizing agent to a fluid, comprising:
a substantially hollow vessel having an inlet passage configured for receiving fluid flow, an outlet passage configured for fluid egress, and an interior chamber configured for receiving fluid from the inlet passage and providing temporary confinement of the fluid therein prior to egress from the outlet passage;
a sanitizing agent operatively disposed in the chamber, the sanitizing agent including one or more reactants which are chemically configured to release a compound having sanitizing properties upon exposure to the fluid in the chamber;
a solution operatively disposed in the chamber of the vessel including a second compound having sanitizing properties, wherein the solution is mixed with fluid in the chamber for egress through the outlet passage; and
a dye indicator operatively associated with the sanitizing agent, for facilitating awareness of the presence of the sanitizing agent in the fluid and the subsequent exhaustion thereof from the fluid.

16. A filter cartridge comprising:
a hollow housing with a filter media chamber defined therein;
a substantially hollow neck mated with the filter media chamber having an inlet port in fluid communication with an inlet passage configured to be in fluid communication with the filter media chamber and an outlet port in fluid communication with an outlet passage configured to be in fluid communication with the filter media chamber, wherein the inlet passage and outlet passage are disposed in the neck and configured to provide dual fluid flow within the neck and independent fluid communication with the filter media chamber;
a sanitizing agent disposed in the filter media chamber, the sanitizing agent including one or more reactants which are chemically configured to release a compound having sanitizing properties upon exposure to the fluid in the filter media chamber;
a tubular member disposed axially in the neck and having a portion with a porous periphery extending into the filter media chamber, the tubular member defining an inner axial passage therein and a radially outer axial passage bounded by the periphery of the tubular member and inner surface of the neck, wherein the outer axial passage and the inner axial passage provide the inlet and outlet passages, respectively; and
a dye indicator operatively associated with the sanitizing agent, for facilitating awareness of the presence of the sanitizing agent in the fluid and the subsequent exhaustion thereof from the fluid.

17. The filter cartridge of claim 16, farther comprising a filtration media disposed along the porous periphery of the portion of the tubular member extending into the filter media chamber.

18. The filter cartridge of claim 17, wherein the sanitizing agent is disposed within the inner axial passage of the portion of the tubular member extending into the filter media chamber.

19. The filter cartridge of claim 17, wherein the sanitizing agent is separated from the filtration media by an inert porous divider.

20. The filter cartridge of claim 16, farther comprising:
a second outlet port in the housing in fluid communication with the filter media chamber and disposed adjacent relative to the position of the sanitizing agent within the filter media chamber for receiving a majority of the fluid exposed to the sanitizing agent.

* * * * *

UNITED STATES PATENT AND TRADEMARK OFFICE
CERTIFICATE OF CORRECTION

| | | |
|---|---|---|
| PATENT NO. | : 7,112,276 B2 | Page 1 of 1 |
| APPLICATION NO. | : 11/096537 | |
| DATED | : September 26, 2006 | |
| INVENTOR(S) | : Thomas D. Holler | |

It is certified that error appears in the above-identified patent and that said Letters Patent is hereby corrected as shown below:

On Title page item 54
In the Title –
    Delete the second occurrence of "OF" and insert --OR--;

Column 1, line 2 –
    Delete "OF" and insert --OR--;

Column 12, line 33 –
    Delete "farther" and insert --further--;

Column 12, line 44 –
    Delete "farther" and insert --further--.

Signed and Sealed this

Twenty-sixth Day of December, 2006

JON W. DUDAS
*Director of the United States Patent and Trademark Office*